(12) United States Patent
Reddy et al.

(10) Patent No.: US 6,833,480 B2
(45) Date of Patent: Dec. 21, 2004

(54) (Z)-STYRYLBENZYLSULFONES AND PHARMACEUTICAL USES THEREOF

(75) Inventors: E. Premkumar Reddy, Villanova, PA (US); M. V. Ramana Reddy, Upper Darby, PA (US)

(73) Assignee: Temple University - Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 10/469,056

(22) PCT Filed: Feb. 26, 2002

(86) PCT No.: PCT/US02/05817

§ 371 (c)(1),
(2), (4) Date: Aug. 21, 2003

(87) PCT Pub. No.: WO02/067913

PCT Pub. Date: Sep. 6, 2002

(65) Prior Publication Data

US 2004/0133030 A1 Jul. 8, 2004

Related U.S. Application Data

(60) Provisional application No. 60/271,762, filed on Feb. 27, 2001.

(51) Int. Cl.[7] ..................... C07C 315/00; C07C 317/00

(52) U.S. Cl. ............................. 568/28; 568/34; 568/35; 568/77

(58) Field of Search ............................. 568/28, 34, 35, 568/77

(56) References Cited

U.S. PATENT DOCUMENTS

| | | | |
|---|---|---|---|
| 2,532,612 A | 12/1950 | Doumani | 568/60 |
| 3,185,743 A | 5/1965 | Combe et al. | 585/638 |
| 3,418,101 A | 12/1968 | Buchholtz et al. | 504/162 |
| 3,463,774 A | 8/1969 | Wilhelm et al. | 540/490 |
| 3,514,386 A | 5/1970 | Oswald et al. | 204/157.73 |
| 3,917,714 A | 11/1975 | Richmond | 568/33 |
| 4,161,407 A | 7/1979 | Campbell | 430/621 |
| 4,386,221 A | 5/1983 | Hyatt et al. | 568/28 |
| 4,937,388 A | 6/1990 | Bushell et al. | 560/56 |
| 5,659,087 A | 8/1997 | Aikins et al. | 568/27 |
| 5,733,909 A | 3/1998 | Black et al. | 514/238.8 |
| 6,201,154 B1 | 3/2001 | Reddy et al. | 568/28 |
| 6,359,013 B1 | 3/2002 | Reddy et al. | 514/710 |
| 6,486,210 B2 | 11/2002 | Reddy et al. | 514/708 |

FOREIGN PATENT DOCUMENTS

| | | |
|---|---|---|
| WO | WO 99/18068 | 4/1999 |
| WO | WO 00/57872 | 10/2000 |
| WO | WO 00/59495 | 10/2000 |
| WO | WO 01/26645 | 4/2001 |

OTHER PUBLICATIONS

U.S. Appl. No. 09/689,281, filed Oct. 11, 2000 of Stephen C. Cosenza et al., for "Method For Protecting Normal Cells From Cytotoxicity Of Chemotherapeutic Agents".
Pub–Med 9734697, Abstracting Griggs JJ., "Reducing the Toxicity of Anticancer Therapy: New Strategies", Leuk Res May 1998;22 Suppl 1:S27–33.
Reddy et al., *Org. Prep. Proc. Int.*, 20(3):205–212 (1988).
Reddy et al., *Phosphorus, Sulfur Silicon Relat. Elem.*, 60:209–214 (1991).
Reddy and Reddy, *Acta Chim. Acad. Sci. Hung.*, 120(4):275–280 (1985).
Reddy and Reddy, *Synthesis* No. 4, 322–323 (1984).
Reddy et al., *Sulfur Lett.*, 7(2):43–48 (1987).
Reddy et al., *Phosphorus, Sulfur, and Silicon*, 53(1–4):285–290 (1990).
Makosza and Krylova, *Liebigs Ann./Recueil*, 2337–2340 (1997).
Reddy et al., *Acta Chim. Hung.*, 131(1):83–92 (1994).
Benati, et al., *J. Org. Chem.*, 59:2818–2823 (1994).
Tanaka et al., Agric. Biol. Chem. 41, 1953–1959, 1977.
Baliah and Rathinasamy, *Indian J. Chem.* (1971), 9:220–225.
Kamigata et al., *Phosphorus and Sulfer*, (1984), 20:139–144.
CA:120:323356 abs of Reddy et al., *Sulf. Lett.* (1993), 16(5–6), 227–35.
CA:100:67921 abs of Takiwa et al., *Chem. Lett.* (1983), 9:1351–4.
CA:123:198103 abs of Riad et al., *Egypt. J. Chem.* (1994), 37(2), 157–71.
CA:124:175763, abs of Reddy et al., *Indian J. Heterocycl. Chem.*, (1995), 5(1), 11–14.
CA:124:146025, abs of Reddy et al., *Indian J. Heterocycl. Chem.* (1995), 4(4), 259–264.
CA:126:166162, abs of Thompson et al., *Cancer Res.*, (1997), 57(2), 267–271.
CA:122:132682 abs of Reddy et al., *Phosphorus, Sulfur Silicon Relat. Elem.* (1994), 90(1–4), 1–10.
CA:124:8731 abs of Reddy et al., *Indian J. Chem. Sect. B: Org Chem. Incl. Med. Chem.* (1995), 34B(9), 816–22.
CA:76:121420 abs of Findlay et al. *Brit J. Dermatol.*, (1971), No. 7, 44–9.
CA:105:133446 abs of Naidu et al., *Proc. Indian Acad. Sci., Chem. Sci* (1985), 95(4), 391–5.
CA:126:185889 abs of Japanese Pat. App. 09–03,037 (Jan. 7, 1997).
CA:132:263142 abs of Hillaire et al., *Pathol. Biol.*(1999), 47(9),895–902.

(List continued on next page.)

Primary Examiner—Deborah D. Carr
(74) Attorney, Agent, or Firm—Drinker Biddle & Reath LLP

(57) ABSTRACT

Substituted (Z)-styrylbenzyl sulfones of the formulae (I, II, III, IV), pharmaceutically acceptable salts thereof, and compositions thereof are provided as cell antiproliferative agents, including, for example, anticancer agents.

20 Claims, No Drawings

OTHER PUBLICATIONS

CA:130:336836 abs of Olson, *Med. Hypotheses*(1999), 51(6), 493–498.

CA:127:33922 abs of Evans and Taylor, *Tetrahedron Lett.* (1997), 3055–3058.

CA:125:327911 abs of Riad et al., *Egypt J. Chem.*(1996), 39(4), 353–364.

CA:120:210378 abs of Cheng and Hwang, *J. Chin. Biochem. Soc.* (1993),22(1), 27–35.

CA:103:141088 abs of Janczewski and Ksiezopolski, *Pol. J. Chem.* (1984), 58(1–2–3), 103–16.

CA:121:256180 abs of Li et al., *Bioorg. Med. Chem. Lett.*(1994),4(13), 1585–90.

Abstracts: 1998, 63(6), 835–841; doi 10.1135/cccc19980835 Abstracting Czechoslovak Chemical Communications, vol. 63, 1998, 63(6), 835–841.

M. V. R. Reddy et al., *Acta Chimica Hungarica* 115 (3), pp. 269–271 (1984).

*Nomenclature of Organic Chemistry*, John Wiley & Sons, Inc., New York, NY, 5$^{th}$ ed., p. 163, p. 221.

D. Bhaskar Reddy et al., *Sulfur Letters*, vol. 13(2), pp. 83–90 (1991).

(Z)-STYRYLBENZYLSULFONES AND PHARMACEUTICAL USES THEREOF

CROSS-REFERENCE TO RELATED APPLICATION

The priority of co-pending U.S. provisional patent application Ser. No. 60/271,762, filed Feb. 27, 2001, is claimed. The entire disclosure of the aforesaid provisional patent application is incorporated herein by reference.

FIELD OF THE INVENTION

The invention relates to compositions and methods for the treatment of proliferative disorders, including but not limited to cancer.

BACKGROUND OF THE INVENTION

New cell antiproliferative agents, and anticancer therapeutics in particular, are needed which are useful in inhibiting proliferation of and/or killing cancer cells. In particular, such agents are needed which are selective in the killing of proliferating cells such as tumor cells, but not normal cells. Antineoplasitc agents are needed which are effective against a broad range of tumor types.

SUMMARY OF THE INVENTION

It is an object of the invention to provide compounds, compositions and therapeutic methods. The biologically active compounds are in the form of certain substituted (Z)-styrylbenzyl sulfones, and pharmaceutically acceptable salts thereof.

It is an object of the invention to provide compounds, compositions and methods for the treatment of cancer and other cell proliferative diseases.

It is an object of the invention to provide compounds which are selective in killing tumor cells but not normal cells.

It is an object of the invention to provide compounds, compositions and methods for inducing neoplastic cells to selectively undergo apoptosis.

In one aspect, the invention is directed to novel compounds of formula I:

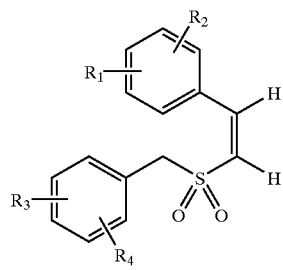

I wherein:

$R_1$ and $R_2$ are independently selected from the group consisting of halogen, C1–C6 alkyl, C1–C6 alkoxy, nitro, cyano, carboxy, carboxy(C1–C3)alkoxy, hydroxy, (C2–C6)hydroxyalkyl, phosphonato, amino, (C1–C6)acylamino, sulfamyl, acetoxy, di(C1–C6)alkylamino(C2–C6 alkoxy) and trifluoromethyl; and $R_3$ and $R_4$ are independently selected from the group consisting of hydrogen, halogen, C1–C6 alkyl, C1–C6 alkoxy, nitro, cyano, carboxy, carboxy(C1–C3)alkoxy, hydroxy, (C2–C6)hydroxyalkyl, phosphonato, amino, (C1–C6)acylamino, sulfamyl, acetoxy, di(C1–C6) alkylamino(C2–C6 alkoxy) and trifluoromethyl; or a pharmaceutically acceptable salt thereof.

In some embodiments, the benzyl nucleus (i.e., the ring system containing $R_3$ and $R_4$) is at least monosubstituted, that is, at least one of $R_3$ and $R_4$ is other than hydrogen.

In some embodiments, $R_1$ and $R_2$ are independently selected from the group consisting of halogen, C1–C6 alkyl, C1–C6 alkoxy, hydroxy and acetoxy, while $R_3$ and $R_4$ are independently selected from the group consisting of hydrogen, halogen, C1–C6 alkyl, C1–C6 alkoxy, nitro and amino.

If the benzyl nucleus is substituted, the substituents in one embodiment are located at the 4- and/or 2-positions, that is, the compounds have the formula II:

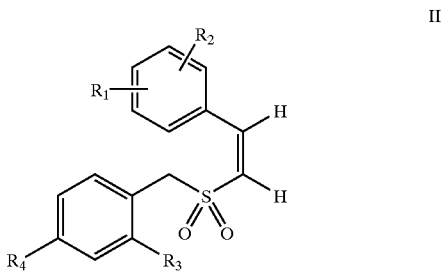

II wherein $R_1$, $R_2$, $R_3$ and $R_4$ are defined as above, wherein at least one or both of $R_3$ and $R_4$ are other than hydrogen. In some embodiments, $R_4$ is other than hydrogen, particularly halogen. In other embodiments, both $R_3$ and $R_4$ are other than hydrogen. According to certain embodiments, one or both of $R_3$ and $R_4$ are halogen, or all of $R_1$, $R_2$, $R_3$ and $R_4$ are halogen.

While any pattern of substitution for $R_1$ and $R_2$ is possible, i.e. 2/4, 2/3, or 3/4, 2/4 substitution is particularly preferred.

According to another embodiment of the invention, (Z)-styryl benzylsulfides are provided which are useful as intermediates in the preparation of (Z)-styryl benzylsulfones. The (Z)-styryl benzylsulfides have the formula:

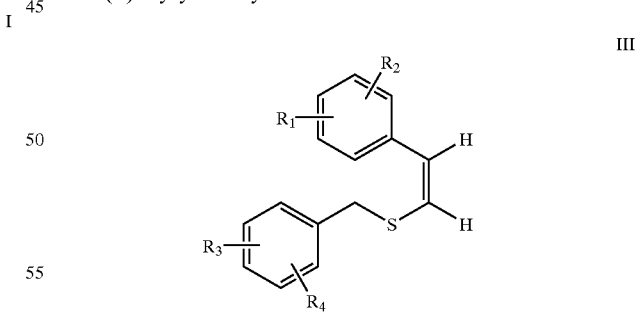

III wherein $R_1$, $R_2$, $R_3$ and $R_4$ are defined as above with respect to formula I.

Selected embodiments of (Z)-styryl benzylsulfide compounds correspond directly to the above-described selected embodiments of (Z)-styryl benzylsulfide compounds, the only difference being the presence of the sulfide group as the precursor of the sulfone group; the latter results from oxidation of the former. For example, the sulfide analogs of the sulfones according to formula III have the formula IV:

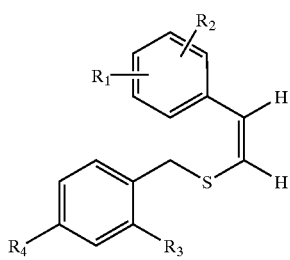

IV wherein $R_1$, $R_2$, $R_3$ and $R_4$ are defined as above with respect to formula III.

According to another embodiment of the invention, pharmaceutical compositions are provided comprising a pharmaceutically acceptable carrier and at least one compound according to formula I, or pharmaceutically acceptable salt thereof.

According to another embodiment of the invention, a method of treating an individual for a cell proliferative disorder comprises administering to said individual an effective amount of at least one compound according to formula I, or pharmaceutically acceptable salt thereof.

According to another embodiment of the invention, a method of inducing apoptosis of tumor cells in an individual afflicted with cancer is provided, comprising administering to said individual an effective amount of at least one compound according to formula I, or pharmaceutically acceptable salt thereof.

The term "alkyl", by itself or as part of another substituent means, unless otherwise stated, a straight or branched chain hydrocarbon radical, including di- and multi-radicals, having the number of carbon atoms designated (i.e. C1–C6 means one to six carbons) and includes straight or branched chain groups. Most preferred is C1–C3 alkyl, particularly ethyl and methyl.

The term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy and the higher homologs and isomers. Preferred are C1–C3 alkoxy, particularly ethoxy and methoxy.

The term "(C2–C6)acylamino" means a radical containing a two to six carbon straight or branched chain acyl group attached to a nitrogen atom via the acyl carbonyl carbon. Examples include —NHC(O)CH$_2$CH$_2$CH$_3$ and —NHC(O)CH$_2$CH$_2$CH$_2$CH$_2$CH$_3$.

The term "carboxy(C1–C3)alkoxy" means a radical in which the carboxy group —COOH is attached to a carbon of a straight or branched chain alkoxy group containing one to three carbon atoms. The radical thus contains up to four carbon atoms. Examples include HOC(O)CH$_2$CH$_2$CH$_2$O— and HOC(O)CH$_2$CH$_2$O—.

The term "di(C1–C6)alkylamino(C2–C6)alkoxy" means (alkyl)$_2$N(CH$_2$)$_n$O— wherein the two alkyl chains connected to the nitrogen atom independently contain from one to six carbon atoms, preferably from one to three carbon atoms, and n is an integer from 2 to 6. Preferably, n is 2 or 3. Most preferably, n is 2, and the alkyl groups are methyl, that is, the group is the dimethylaminoethoxy group, (CH3)$_2$NCH$_2$CH$_2$O—.

The terms "halo" or "halogen" by themselves or as part of another substituent mean, unless otherwise stated, a fluorine, chlorine, bromine, or iodine atom.

The term "hydroxyalkyl" means an alkyl radical wherein one or more of the carbon atoms is substituted with hydroxy. Examples include —CH$_2$CH(OH)CH$_3$ and —CH$_2$CH$_2$OH.

The term "phosphonato" means the group —PO(OH)$_2$.

The term "sulfamyl" means the group —SO$_2$NH$_2$.

By "substituted" means that an atom or group of atoms has replaced hydrogen as the substituent attached to another group.

By "subject" is meant an animal or a human being.

DETAILED DESCRIPTION OF THE INVENTION

According to the present invention, certain (Z)-styrylbenzyl sulfones and pharmaceutically acceptable salts thereof are provided for inhibiting proliferation of cancer cells. They are believed to be effective in killing tumor cell types without killing normal cells. The compounds of the invention are believed to induce apoptosis of tumor cells and cell death. The compounds are believed effective against a broad range of tumor types, including but not limited to the following: breast, prostate, ovarian, lung, colorectal, brain (i.e, glioma) and renal. The compounds are also believed effective against leukemic cells.

The compounds of the invention are also believed useful in the treatment of non-cancer cell proliferative disorders, including but not limited to the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

Compounds having a carbon-carbon double bond are characterized by cis-trans isomerism. Such compounds are named according to the Cahn-Ingold-Prelog system, the IUPAC 1974 Recommendations, Section B: Stereochemistry, in *Nomenclature of Organic Chemistry*, John Wiley & Sons, Inc., New York, N.Y., 4th ed., 1992, p. 127–138. Steric relations around a double bond are designated as "Z" or "E". The compounds of the present invention have the "Z" configuration.

The substituted (Z)-styrylbenzylsulfones of the invention are prepared by the nucleophilic addition of the appropriate thiol to substituted phenylacetylene with subsequent oxidation of the resulting sulfide by hydrogen peroxide to yield the Z-styrylbenzylsulfone. In the first phase of the synthesis, a substituted or unsubstitued sodium benzylthiolate, prepared from an appropriate substituted or unsubstitued sodium benzyl mercaptan, is allowed to react with the appropriate substituted phenylacetylene forming the pure Z-isomer of the corresponding substituted (Z-styrylbenzylsulfide in good yield. In the second step of the synthesis, the substituted (Z)-styrylbenzylsulfide Intermediate is oxidized to the corresponding sulfone in the pure Z-isomeric form by treatment with an oxidizing agent, such as hydrogen peroxide.

The following is a more detailed two-part synthesis procedure for preparing the substituted (Z)-styrylbenzylsulfones:

General Procedure: Synthesis of Substituted (Z)-styryl Benzylsulfones

A. To a cooled stirred solution (40° C.) of a substituted styrene (0.5 mol) in chloroform (200 ml) is added dropwise a solution of bromine (0.5 mol) in chloroform (100 ml). After the addition is complete, the contents of the flask are stirred for an additional 30 minutes. Removal of chloroform in rotavapor yields a crystalline solid of a substituted styrene dibromide.

B. A solution of potassium hydroxide (85 g) in rectified spirit (400 ml) is cooled to room temperature (25° C.) and the substituted styrene dibromide (0.33 mol) is added in portions to control the exothermic reaction. After the addition is complete, the reaction mixture is heated to reflux for 6 hours. The contents are then cooled and poured into water (1000 ml). The separated substituted phenylacetylene is purified either by distillation (in case of liquids) or recrystallization (in case of solids).

C. To a refluxing methanolic solution of a substituted or unsubstituted sodium benzylthiolate prepared from 460 mg (0.02 g atom) of (i) sodium, (ii) substituted or unsubstituted sodium benzyl mercaptan (0.02 mol) and (iii) 80 ml of absolute methanol, is added a freshly distilled substituted phenylacetylene. The mixture is refluxed for 20 hours, cooled and then poured on crushed ice. The crude product is filtered, dried and recrystallized from methanol or aqueous methanol to yield pure substituted (Z)-styrylbenzylsulfide.

D. An ice cold solution of a substituted (Z)-styrylbenzylsulfide (3 g) in 30 ml of glacial acetic acid is treated with 7.5 ml of 30% hydrogen peroxide. The reaction mixture is refluxed for 1 hour and poured onto crushed ice. The solid separated is filtered, dried and recrystallized from 2-propanol to yield a pure substituted (Z)-styrylbenzylsulfone. The purity of the compound is ascertained by TLC and geometrical configuration is assigned by IR and NMR spectral data.

The compounds of the present invention may take the form or pharmaceutically acceptable salts. The term "pharmaceutically acceptable salts", embraces salts commonly used to form alkali metal salts and to form addition salts of free acids or free bases. The nature of the salt is not critical, provided that it is pharmaceutically-acceptable. Suitable pharmaceutically acceptable acid addition salts may be prepared from an inorganic acid or from an organic acid. Examples of such inorganic acids are hydrochloric, hydrobromic, hydrolodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, salicyclic, galactaric and galacturonic acid. Suitable pharmaceutically acceptable base addition salts of compounds of formula I include metallic salts made from calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of formula I by reacting, for example, the appropriate acid or base with the compound of formula I.

The compounds of the invention may be administered to individuals (mammals, including animals and humans) afflicted with cancer.

The compounds are also useful in the treatment of non-cancer cell proliferative disorders, that is, cell proliferative disorders which are characterized by benign indications. Such disorders may also be known as "cytoproliferative" or "hyperproliferative" in that cells are made by the body at an typically elevated rate. Such disorders include, but are not limited to, the following: hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

The specific dose of compound according to the invention to obtain therapeutic benefit will, of course, be determined by the particular circumstances of the individual patient including, the size, weight, age and sex of the patient, the nature and stage of the disease, the aggressiveness of the disease, and the route of administration. For example, a daily dosage of from about 0.05 to about 50 mg/kg/day may be utilized. Higher or lower doses are also contemplated.

The compounds of the invention may be administered for therapeutic effect by any route, including oral and parenteral administration. Parenteral administration includes, for example, intravenous, intramuscular, intraarterial, intraperitoneal, intranasal, rectal, intravaginal, intravesical (e.g., into the bladder), intradermal, topical or subcutaneous administration. Also contemplated within the scope of the invention is the instillation of drug in the body of the patient in a controlled formulation, with systemic or local release of the drug to occur at a later time. For example, the drug may localized in a depot for controlled release to the circulation, or for release to a local site of tumor growth.

The compounds of the invention may be administered in the form of a pharmaceutical composition, in combination with a pharmaceutically acceptable carrier. The active ingredient in such formulations may comprise from 0.1 to 99.99 weight percent. By "pharmaceutically acceptable carrier" is meant any carrier, diluent or excipient which is compatible with the other ingredients of the formulation and to deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Ed., (1990) Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidizing agents and preservatives may also be added. Suitable antioxidizing agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The practice of the invention is illustrated by the following non-limiting examples. Each compound is prepared by following the General Procedure, above. For brevity, only the principal reactants are listed in each example, it being understood that the principal reactants are made from precursors as set forth in the General Procedure, and the combined under the conditions set forth in the General Procedure.

EXAMPLE 1
(Z)-2,4-difluorostyryl-4-chlorobenzylsulfone

A solution of 2,4-difluorophenylacetylene (0.02 mol), 4-chlorobenzyl mercaptan (0.02 mol) and metallic sodium (0.02 g atom) is subjected to the General Procedure to form (Z)-2,4-difluorostyryl-4-chlorobenzylsulfide. The title compound is obtained following oxidation of the sulfide, according to the General Procedure.

EXAMPLE 2
(Z)-2,3-dichlorostyryl-4-bromobenzylsulfone

A solution of 2,3-dichlorophenylacetylene (0.02 mol), 4-bromobenzyl mercaptan (0.02 mol) and metallic sodium (0.02 g atom) is subjected to the General Procedure to form (Z)-2,3-dichlorostyryl-4-bromobenzylsulfide. The title compound is obtained following oxidation of the sulfide, according to the General Procedure.

EXAMPLE 3
(Z)-2,4-dichlorostyryl-4-fluorobenzylsulfone

A solution of 2,4-dichlorophenylacetylene (0.02 mol), 4-fluorobenzyl mercaptan (0.02 mol) and metallic sodium (0.02 g atom) is subjected to the General Procedure to form (Z)-2,4-dichlorostyryl-4-fluorobenzylsulfide. The title compound is obtained following oxidation of the sulfide, according to the General Procedure.

EXAMPLE 4
(Z)-2,4-dimethylstyryl-4-chlorobenzylsulfone

A solution of 2,4-dimethylphenylacetylene (0.02 mol), 4-chlorobenzyl mercaptan (0.02 mol) and metallic sodium (0.02 g atom) is subjected to the General Procedure to form (Z)-2,4-dimethylstyryl-4-chlorobenzylsulfide. The title compound is obtained following oxidation of the sulfide, according to the General Procedure.

EXAMPLE 5
(Z)-2,3-dimethylstyryl-4-bromobenzylsulfone

A solution of 2,3-dimethylphenylacetylene (0.02 mol), 4-bromobenzyl mercaptan (0.02 mol) and metallic sodium (0.02 g atom) is subjected to the General Procedure to form (Z)-2,3-dimethylstyryl-4-bromobenzylsulfide. The title compound is obtained following oxidation of the sulfide, according to the General Procedure.

EXAMPLE 6
(Z)-2,4-dimethoxystyryl-4-fluorobenzylsulfone

A solution of 2,4-dimethoxyphenylacetylene (0.02 mol), 4-fluorobenzyl mercaptan (0.02 mol) and metallic sodium (0.02 g atom) is subjected to the General Procedure to form (Z)-2,4-dimethoxystyryl-4-fluorobenzylsulfide. The title compound is obtained following oxidation of the sulfide, according to the General Procedure.

EXAMPLE 7
(Z)-2,4-difluorostyryl-2,4-dichlorobenzylsulfone

A solution of 2,4-difluorophenylacetylene (0.02 mol), 2,4-dichlorobenzyl mercaptan (0.02 mol) and metallic sodium (0.02 g atom) is subjected to the General Procedure to form (Z)-2,4-difluorostyryl-2,4-dichlorobenzylsulfide. The title compound is obtained following oxidation of the sulfide, according to the General Procedure.

EXAMPLE 8
(Z)-2,3-dichlorostyryl-2-chloro-4-fluorobenzylsulfone

A solution of 2,3-dichlorophenylacetylene (0.02 mol), 2-chloro-4-fluorobenzyl mercaptan (0.02 mol) and metallic sodium (0.02 g atom) is subjected to the General Procedure to form (Z)-2,3-dichlorostyryl-2-chloro-4-fluorobenzylsulfide. The title compound is obtained following oxidation of the sulfide, according to the General Procedure.

EXAMPLE 9
(Z)-2,4-dichlorostyryl-2-chloro-4-methylbenzylsulfone

A solution of 2,4-dichlorophenylacetylene (0.02 mol), 2-chloro-4-methylbenzyl mercaptan (0.02 mol) and metallic sodium (0.02 g atom) is subjected to the General Procedure to form (Z)-2,4-dichlorostyryl-2-chloro-4-methylbenzylsulfide. The title compound is obtained following oxidation of the sulfide, according to the General Procedure.

EXAMPLE 10
(Z)-2,4-dimethylstyryl-2,4-dimethylbenzylsulfone

A solution of 2,4-dimethylphenylacetylene (0.02 mol) and 2,4-dimethylbenzyl mercaptan (0.02 mol) and metallic sodium (0.02 g atom) is subjected to the General Procedure to form (Z)-2,4-dimethylstyryl-2,4-dimethylbenzylsulfide. The title compound is obtained following oxidation of the sulfide, according to the General Procedure.

EXAMPLE 11
(Z)-2,3-dimethylstyryl-2-chloro-4-methoxybenzylsulfine

A solution of 2,3-dimethylphenylacetylene (0.02 mol), 2-chloro-4-methoxybenzyl mercaptan (0.02 mol) and metallic sodium (0.02 g atom) is subjected to the General Procedure to form (Z)-2,3-dimethylstyryl-2-chloro-4-methoxybenzylsulfide. The title compound is obtained following oxidation of the sulfide, according to the General Procedure.

EXAMPLE 12
(Z)-2,4-dimethoxystyryl-2,4-dimethoxybenzylsulfone

A solution of 2,4-dimethoxyphenylacetylene (0.02 mol), 2,4-dimethoxybenzyl mercaptan (0.02 mol) and metallic sodium (0.02 g atom) is subjected to the General Procedure to form (Z)-2,4-dimethoxystyryl-2,4-dimethoxybenzylsulfide. The title compound is obtained following oxidation of the sulfide, according to the General Procedure.

EXAMPLE 13
(Z)-3-methoxy-4-acetoxystyryl-2,4-dichlorobenzylsulfone

A solution of 3-methoxy-4-acetoxyphenylacetylene (0.02 mol), 2,4-dichlorobenzyl mercaptan (0.02 mol) and metallic sodium (0.02 g atom) is subjected to the General Procedure to form (Z)-3-methoxy-4-acetoxystyryl-2,4-dichlorobenzylsulfide. The title compound is obtained following oxidation of the sulfide, according to the General Procedure.

EXAMPLE 14
(Z)-3-methoxy-4-acetoxystyryl-2-chloro-4-methoxybenzylsulfone

A solution of 3-methoxy-4-acetoxyphenylacetylene (0.02 mol), 2-chloro-4-methoxybenzyl mercaptan (0.02 mol) and metallic sodium (0.02 g atom) is subjected to the General Procedure to form (Z)-3-methoxy-4-acetoxystyryl-2-chloro-4-methoxybenzylsulfide. The title compound is obtained following oxidation of the sulfide, according to the General Procedure.

EXAMPLE 15
(Z)-3-methoxy-4-hydroxystyryl-4-methoxybenzylsulfone

A solution of 3-methoxy-4-hydroxyphenylacetylene (0.02 mol), 4-methoxybenzyl mercaptan (0.02 mol) and metallic sodium (0.02 g atom) is subjected to the General Procedure to form (Z)-3-methoxy-4-hydroxystyryl-4-methoxybenzylsulfide. The title compound is obtained following oxidation of the sulfide, according to the General Procedure.

EXAMPLE 16
(Z)-3-methoxy-4-hydroxystyryl-4-methylbenzylsulfone

A solution of 3-methoxy-4-hydroxyphenylacetylene (0.02 mol), 4-methylbenzyl mercaptan (0.02 mol) and metallic sodium (0.02 g atom) is subjected to the General Procedure to form (Z)-3-methoxy-4-hydroxystyryl-4-methylbenzylsulfide. The title compound is obtained following oxidation of the sulfide, according to the General Procedure.

EXAMPLE 17
(Z)-3-methoxy-4-hydroxystyryl-2-chloro-4-fluorobenzylsulfone

A solution of 3-methoxy-4-hydroxyphenylacetylene (0.02 mol), 2-chloro-4-fluorobenzyl mercaptan (0.02 mol) and metallic sodium (0.02 g atom) is subjected to the General Procedure to form (Z)-3-methoxy-4-hydroxystyryl-2-chloro-4-fluorobenzylsulfide. The title compound is obtained following oxidation of the sulfide, according to the General Procedure.

EXAMPLE 18
(Z)-3,4-dihydroxystyryl-2-chloro-4-methoxybenzylsulfone

A solution of 3,4-dihydroxyphenylacetylene (0.02 mol), 2-chloro-4-methoxybenzyl mercaptan (0.02 mol) and metallic sodium (0.02 g atom) is subjected to the General Procedure to form (Z)-3,4-dihydroxystyryl-2-chloro-4-methoxybenzylsulfide. The title compound is obtained following oxidation of the sulfide, according to the General Procedure.

EXAMPLE 19
(Z)-2,4-difluorostyryl-2-aminobenzylsulfone

A solution of 2,4-difluorophenylacetylene (0.02 mol), 2-aminobenzyl mercaptan (0.02 mol) and metallic sodium (0.02 g atom) is subjected to the General Procedure to form (Z)-2,4-difluorostyryl-2-aminobenzylsulfide. The title compound is obtained following oxidation of the sulfide, according to the General Procedure.

EXAMPLE 20
(Z)-4-phosphonatostyryl-2-chloro-4-methoxybenzylsulfone

A solution of 4-phosphonatophenylacetylene (0.02 mol), 2-chloro-4-methoxybenzyl mercaptan (0.02 mol) and metallic sodium (0.02 g atom) is subjected to the General Procedure to form (Z)-4-phosphonatostyryl-2-chloro-4-methoxybenzylsulfide. The title compound is obtained following oxidation of the sulfide, according to the General Procedure.

EXAMPLE 21
Effect of Substituted (Z)-Styrylbenzylsulfones on Tumor Cell Lines The effect of the (Z)-styrylbenzylsulfones on normal fibroblasts and on tumor cells is demonstrated by the assay described by Latham et al., *Oncogene* 12:827–837 (1996). Normal diploid lung human fibroblasts (HFL-1) or tumor cells (e.g., prostate, colo-rectal, breast, glial, pancreatic ovarian or leukemic) are plated in 6-well dishes at a cell density of $1.0 \times 10^5$ cells per 35-mm$^2$ well. The plated cells are treated 24 hours later with various concentrations of (Z)-styrylbenzylsulfone dissolved in dimethyl sulfoxide (DMSO). The total number of viable cells is determined 96 hours later by trypsinizing the wells and counting the number of viable cells, as determined by trypan blue exclusion, using a hemacytometer. Normal HFL are treated with the same compounds under the same conditions of concentration and time.

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

What is claimed is:

1. A compounds of the formula:

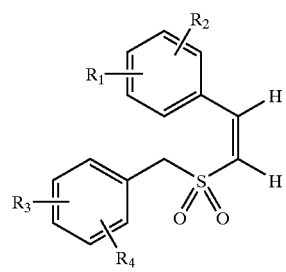

wherein:

$R_1$ and $R_2$ are independently selected from the group consisting of halogen, C1–C6 alkyl, C1–C6 alkoxy, nitro, cyano, carboxy, carboxy(C1–C3)alkoxy, hydroxy, (C2–C6)hydroxyalkyl, phosphonato, amino, (C1–C6)acylamino, sulfamyl, acetoxy, di(C1–C6)alkylamino(C2–C6 alkoxy) and trifluoromethyl; and $R_3$ and $R_4$ are independently selected from the group consisting of hydrogen, halogen, C1–C6 alkyl, C1–C6 alkoxy, nitro, cyano, carboxy, carboxy(C1–C3)alkoxy, hydroxy, (C2–C6)hydroxyalkyl, phosphonato, amino, (C1–C6)acylamino, sulfamyl, acetoxy, di(C1–C6)alkylamino(C2–C6 alkoxy) and trifluoromethyl; or a pharmaceutically acceptable salt thereof.

2. A compound according to claim 1 wherein at least one of $R_3$ and $R_4$ is other than hydrogen, or a pharmaceutically acceptable salt thereof.

3. A compound according to claim 2 wherein $R_1$ and $R_2$ are independently selected from the group consisting of halogen, C1–C6 alkyl, C1–C6 alkoxy, hydroxy and acetoxy, and $R_3$ and $R_4$ are independently selected from the group consisting of hydrogen, halogen, C1–C6 alkyl, C1–C6 alkoxy and amino, or a pharmaceutically acceptable salt thereof.

4. A compound according to claim 3 of the formula:

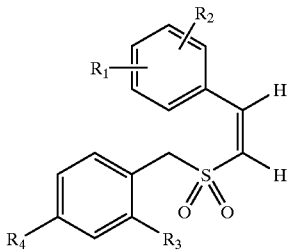

wherein $R_1$ and $R_2$ are independently selected from the group consisting of halogen, C1–C6 alkyl, C1–C6 alkoxy, hydroxy and acetoxy, and $R_3$ and $R_4$ are selected from the group consisting of hydrogen, halogen, C1–C6 alkyl, C1–C6 alkoxy and amino, or a pharmaceutically acceptable salt thereof.

5. A compound according to claim 4 wherein $R_4$ is other than hydrogen, or a pharmaceutically acceptable salt thereof.

6. A compound according to claim 5 wherein $R_3$ and $R_4$ are other than hydrogen, or a pharmaceutically acceptable salt thereof.

7. A pharmaceutical composition comprising a pharmaceutically acceptable carrier and at least one compound according to claim 1.

8. A pharmaceutical composition comprising a pharmaceutically acceptable carrier at least one compound according to claim 2.

9. A pharmaceutical composition comprising a pharmaceutically acceptable carrier at least one compound according to claim 3.

10. A method of treating an individual for a cell proliferative disorder comprising administering to said individual an effective amount of at least one compound according to claim 1.

11. A method of treating an individual for a cell proliferative disorder comprising administering to said individual an effective amount of at least one compound according to claim 2.

12. A method of treating an individual for a cell proliferative disorder comprising administering to said individual an effective amount of at least one compound according to claim 3.

13. A method according to claim 10 wherein the cell proliferative disorder is selected from the group consisting of hemangiomatosis in new born, secondary progressive multiple sclerosis, chronic progressive myelodegenerative disease, neurofibromatosis, ganglioneuromatosis, keloid formation, Pagets Disease of the bone, fibrocystic disease of the breast, Peronies and Duputren's fibrosis, restenosis and cirrhosis.

14. A method according to claim 10 wherein the cell proliferative disorder is cancer.

15. A method of according to claim 14 wherein the cancer is selected from the group consisting of ovarian, breast, prostate, lung, renal, colorectal and brain cancers, or the cancer is a leukemia.

16. A method of inducing apoptosis of tumor cells in an individual afflicted with cancer comprising administering to said individual an effective amount of at least one compound according to claim 1.

17. A compound of the formula:

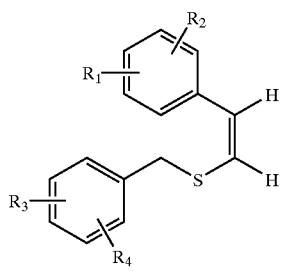

wherein:

$R_1$ and $R_2$ are independently selected from the group consisting of halogen, C1–C6 alkyl, C1–C6 alkoxy, nitro, cyano, carboxy, carboxy(C1–C3)alkoxy, hydroxy, (C2–C6)hydroxyalkyl, phosphonato, amino, (C1–C6)acylamino, sulfamyl, acetoxy, di(C1–C6) alkylamino(C2–C6 alkoxy) and trifluoromethyl; and $R_3$ and $R_4$ are independently selected from the group consisting of hydrogen, halogen, C1–C6 alkyl, C1–C6 alkoxy, nitro, cyano, carboxy, carboxy(C1–C3)alkoxy, hydroxy, (C2–C6)hydroxyalkyl, phosphonato, amino, (C1–C6)acylamino, sulfamyl, acetoxy, di(C1–C6) alkylamino(C2–C6 alkoxy) and trifluoromethyl.

18. A compound according to claim 17 wherein at least one of $R_3$ and $R_4$ is other than hydrogen.

19. A compound according to claim 18 wherein $R_1$ and $R_2$ are independently selected from the group consisting of halogen, C1–C6 alkyl, C1–C6 alkoxy, hydroxy and acetoxy, and $R_3$ and $R_4$ are selected from the group consisting of hydrogen, halogen, C1–C6 alkyl, C1–C6 alkoxy and amino.

20. A compound according to claim 19 of the formula:

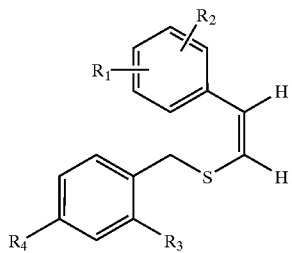

wherein $R_1$ and $R_2$ are independently selected from the group consisting of halogen, C1–C6 alkyl, C1–C6 alkoxy, hydroxy and acetoxy, and $R_3$ and $R_4$ are selected from the group consisting of hydrogen, halogen, C1–C6 alkyl, C1–C6 alkoxy and amino.

* * * * *